United States Patent [19]
Hirata et al.

[11] 3,936,497
[45] Feb. 3, 1976

[54] PROCESS FOR PREPARATION OF 4,4'-DIAMINOSTILBENE-2,2'-DISULFONIC ACID OR SALTS THEREOF

[75] Inventors: Naonori Hirata, Toyonaka; Masatoshi Matsuo, Takatsuki, both of Japan

[73] Assignee: Sumitomo Chemical Company, Limited, Osaka, Japan

[22] Filed: Dec. 2, 1974

[21] Appl. No.: 528,658

[30] Foreign Application Priority Data
Dec. 3, 1973 Japan.............................. 48-136563
Dec. 5, 1973 Japan.............................. 48-136998

[52] U.S. Cl. ................................................ 260/510
[51] Int. Cl.² ........................................ C07C 143/56
[58] Field of Search ...................... 260/510, 508, 580

[56] References Cited
UNITED STATES PATENTS

| | | | |
|---|---|---|---|
| 2,784,220 | 3/1957 | Spiegler et al. .................... | 260/510 |
| 2,933,503 | 4/1960 | Clark et al. ......................... | 260/580 |
| 3,067,253 | 12/1962 | Dietzier et al. ..................... | 260/575 |
| 3,148,217 | 9/1964 | Freyermuth et al. ............... | 260/580 |
| 3,350,452 | 10/1967 | Rylander et al. ................... | 260/580 |
| 3,555,071 | 1/1971 | Rao et al. ........................... | 260/580 |
| 3,862,245 | 1/1975 | Greco ................................. | 260/580 |

*Primary Examiner*—James O. Thomas, Jr.
*Assistant Examiner*—Nicky Chan
*Attorney, Agent, or Firm*—Stevens, Davis, Miller & Mosher

[57] ABSTRACT

Disodium 4,4'-diaminostilbene-2,2'-disulfonate is prepared by catalytically reducing disodium 4,4'-dinitrostilbene-2,2'-disulfonate with hydrogen in the presence of a nickel catalyst, either (1) in an alcohol medium in which a water content of the reaction system is 3 % by weight or below based on the system before the beginning of the reaction, or (2) in an aqueous medium in which pH of the system is adjusted to a range from 5 to 10 using a buffer.

7 Claims, No Drawings

PROCESS FOR PREPARATION OF 4,4'-DIAMINOSTILBENE-2,2'-DISULFONIC ACID OR SALTS THEREOF

The present invention relates to an improvement in the preparation of disodium 4,4'-diaminostilbene-2,2'-disulfonate (hereinafter referred to as "DAS") by a catalytic reduction of disodium 4,4'-dinitrostilbene-2,2'-disulfonate (hereinafter referred to as "DNS").

DAS is very important as an intermediate for the preparation of dyestuffs, and of particularly fluorescent brightening agents, and at present is generally prepared by an iron reduction process. Since the method requires a large amount of iron, however, separation of DAS from iron sludge after completion of the reaction is very troublesome, and in addition treatment of the iron sludge is also very labor-consuming. Therefore, the method is not suitable for a mass production.

There is a catalytic reduction process as an alternative method free from these defects. According to the method, DAS can be prepared using only hydrogen and a catalytic amount of metal, so that the method has no such troubles as encountered in the iron reduction process. The catalytic reduction of DNS, however, has essentially serious problems. For example, it produces a large amount of dibenzyl derivatives as by-products because DNS has an ethylenic linkage which is very easily hydrogenated like nitro group. Furthermore, it produces colored products which are responsible for very low quality of the resulting DAS.

U.S. Pat. No. 2,784,220 and Japanese Patent Publication No. 815/1973 disclose the preparation of high-purity DAS using a platinum or palladium catalyst, but the method disclosed in the above two patents has aforesaid serious problems to be solved. In addition, the method includes the operation of adding an aqueous DNS solution to the reaction system at such a rate as does not allow the unreacted DNS to be present in excess, which is very troublesome and requires a reaction time as long as 25 hours. Therefore, the method has a very low industrial value.

With the object of producing a high-quality DAS satisfactory as an intermediate for the preparation of fluorescent brightening agents in a high concentration and a high yield and in a short time, and moreover of establishing a simple manufacturing method thereof, the inventors have extensively studied the catalytic reduction process on its various conditions including catalysts, reaction solvents, reaction temperatures, reaction pressures and operations.

The present invention provides a process for preparing disodium 4,4'-diaminostilbene-2,2'-disulfonate which comprises reducing disodium 4,4'-dinitrostilbene-2,2'-disulfonate with hydrogen in the presence of a nickel catalyst, either (1) in an alcohol medium wherein a water content of the reaction system before the beginning of the reaction is 3% by weight or below, or (2) in an aqueous medium, wherein pH of the reaction system is adjusted to a range from 5 to 10 using a buffer throughout the reaction.

A first embodiment of the present invention will be illustrated as follows:

The catalytic reduction in an alcohol is carried out in a pressure vessel or autoclave. The alcohol used includes a lower aliphatic alcohol such as methyl alcohol, ethyl alcohol, isopropyl alcohol, n-propyl alcohol, n-butyl alcohol, isobutyl alcohol, sec-butyl alcohol and tert-butyl alcohol alone or in combination thereof.

The catalyst used may be any of nickel compounds and is particularly preferably wet-developed nickel such as Raney nickel or Urushibara nickel [Bull. Chem. Soc. Japan, 25, 280 (1952); 27, 480 (1954)] or dry nickel.

The amount of the catalyst used is at least 0.1% by weight, preferably at least 0.5% by weight based on DNS. The reaction temperature depends upon amounts of catalyst and DNS and hydrogen pressure, and for a higher reaction rate and a shorter reaction time, a temperature range from 20° to 200°C, and particularly from 30° to 170°C, is preferred. It is of course sufficiently possible to carry out the reaction out of the above temperature range.

For the hydrogen pressure (internal pressure), a pressure of at least 0.5 kg/cm$^2$ is sufficient, and particularly a pressure of at least 1 kg/cm$^2$ is advantageous for shortening the reaction time.

An upper limit of the pressure is not particularly limited, but a pressure of 30 kg/cm$^2$ is sufficient to achieve the object of the present invention.

The concentration of DNS in the reaction system is at least 1% by weight based on the weight of the system, and particularly preferably from 10 to 30% by weight in view of economy and solubility of DNS.

The reaction time depends upon an amount of catalyst, hydrogen pressure, reaction temperature and DNS concentration, but it is usually from 30 minutes to 8 hours.

Before starting the reaction, a water content of the reaction system must be reduced to 3% by weight or less. If the content exceeds 3% by weight, conversion into DAS of the colored diazo compound intermediately produced from DNS becomes slow so remarkably that the diazo compound remains unreacted in an increasing amount and at the same time a large amount of dibenzyl compounds are produced as by-products. Thus, the DAS produced is disadvantageously low in yield and poor in quality.

Reducing the water content to 3% by weight or less before the beginning of the reaction may be carried out by previously removing water from each of catalyst, DNS and alcohol according to a conventional manner such as filtration, drying and distillation, or by distilling off water from the mixture, if necessary.

According to the process of the present invention, only nitro group is selectively reduced and the formation of red-colored by-products can be prevented.

The process of the present invention is very unique and any other combination of catalyst and solvent can not achieve the object of the present invention. For example, in combined systems such as platinum-water, palladium-water, platinum-alcohols and palladium-alcohols, the reaction does not proceed at all, or even if proceeds, it produces dibenzyl derivatives as by-products in a proportion as high as 50% based on the total product or a large amount of red-colored by-products and no effect comparable to the process of the present invention can be obtained.

The present invention can give the surprising effect that formation of dibenzyl derivatives and red-colored materials is inhibited to less than 0.01% and to zero, respectively, and that the yield of DAS is increased to more than 97%.

Superiority of the present invention will become more apparent from the follow-up result of the above two patents that the dibenzyl derivatives and red-colored products are produced in a proportion of 20 to 50% and 5 to 10% based on the total product, respectively.

Next, a second embodiment of the present invention will be illustrated.

The catalytic reduction in aqueous medium according to the present invention is also carried out in a pressure vessel or autoclave.

The buffer used in the process of the present invention includes compositons of phosphoric acid, boric acid or organic acid series. The compositions of phosphoric acid series comprise a mixture of phosphoric acid, alkali hydrogen phosphates and/or alkali dihydrogen phosphates, if desired, together with at least one member of alkali hydroxides, alkali hydrogen carbonates, borax, boric acid, hydrochloric acid, acetic acid, citric acid and diethyl barbiturate. Favorable examples are as follows:

(1) { Potassium dihydrogen phosphate (or sodium salt)
      Disodium hydrogen phosphate (or dipotassium salt)
(2) { Potassium dihydrogen phosphate (or sodium salt)
      Sodium hydrogen carbonate (or potassium salt)
(3) { Potassium dihydrogen phosphate (or sodium salt)
      Sodium hydroxide (or potassium salt)
(4) { Potassium dihydrogen phosphate (or sodium salt)
      Borax
(5) { Disodium hydrogen phosphate (or dipotassium salt)
      Citric acid
(6) { Sodium dihydrogen phosphate (or potassium salt)
      Borax
(7) { Dipotassium hydrogen phosphate (or disodium salt)
      Citric acid
(8) { Phosphoric acid, acetic acid and boric acid
      Sodium hydroxide (or potassium salt)
(9) { Potassium dihydrogen phosphate (or sodium salt), citric acid, boric acid, diethyl barbiturate and hydrochloric acid
      Sodium hydroxide (or potassium salt)

The buffer compositions of boric acid series comprise a mixture of boric acid and/or borax with at least one member of alkali chlorides, alkali hydroxides, alkali carbonates, succinic acid and alkali hydrogen citrates. Favorable examples are as follows:

(10) { Boric acid
       Potassium chloride (or sodium salt)
       Sodium carbonate (or potassium salt)
(11) { Boric acid
       Potassium chloride (or sodium salt)
       Sodium hydroxide (or potassium salt)
(12) { Borax
       Boric acid
       Sodium chloride (or potassium salt)
(13) { Borax
       Succinic acid
(14) { Borax
       Potassium hydrogen citrate (or sodium salt)
(15) { Borax
       Sodium carbonate (or potassium salt)

Further, the buffer compositions of organic acid series used according to the present invention comprise a mixture of glycine, alkali citrates, acetic acid, alkali acetates, alkali diethyl barbiturates and/or alkali dimethylaminoacetates together with at least one member of alkali chlorides, alkali hydroxides and hydrochloric acid. Favorable examples are as follows:

(16) { Glycine
       Sodium chloride (or potassium salt)
       Sodium hydroxide (or potassium salt)
(17) { Sodium citrate (or potassium salt)
       Sodium hydroxide (or potassium salt)
(18) { Acetic acid
       Sodium acetate (or potassium salt)
(19) { Sodium diethyl barbiturate (or potassium salt)
       Sodium acetate (or potassium salt)
       Hydrochloric acid
(20) { Sodium diethyl barbiturate (or potassium salt)
       Hydrochloric acid
(21) { Sodium dimethylaminoacetate (or potassium salt)
       Hydrochloric acid The reaction according to the present invention proceeds smoothly at pH of at least 5, and preferably 5 to 10. A pH value of less than 5 leads to dissolution of the catalyst, inhibiting progress of the reaction remarkably, while a pH value of more than 10 causes not only formation of a large amount of red-colored by-products but also elongation of reaction time and reduction in yield. Therefore, composition of the abovementioned buffer solution must be adjusted to keep the pH within the above range.

When the buffer is not used, the pH fluctuates very widely before, during and after reaction, so that the reaction is very complicated and the preparation of dibenzyl derivatives and red-colored by-products is promoted. These side reactions can be well inhibited by using the buffer.

In this process, the phosphoric acid, boric acid and organic acid series compositions act not only as a buffer but also as a promotor for nickel catalyst, thus promoting formation of DAS and inhibiting formation of dibenzyl derivatives.

As the nickel catalysts used according to the present invention, common nickel catalysts are sufficient, but Raney nickel or Urushibara nickel is particularly preferred in view of reaction rate and reaction temperature.

For Raney nickel catalysts, there are several grades, W-1 to W-7, any of which may be used, but W-7, the most active grade, is particularly preferred. In case of Urushibara nickel, both the grades, A and B, may be used. The amount of catalyst used is at least 0.1% by weight, and preferably at least 0.5% by weight, based on DNS.

The reaction temperature is 20° to 200°C, and preferably 50° to 180°C, and at a temperature of less than 20°C the reaction time is prolonged while at a temperature of more than 200°C the yield of DAS is somewhat reduced.

The hydrogen pressure is at least 1 kg/cm$^2$, and preferably 3 to 30 kg/cm$^2$. At below 1 kg/cm$^2$, the reaction time is prolonged while an upper limit is not particularly present, but 30 kg/cm$^2$ is sufficient to carry out the present invention.

AS for the concentration of DNS, a concentration of at least 1% by weight is sufficient, but that of 10 to 30% by weight is most preferred in view of economy and solubility of DNS in water.

The reaction time is affected largely by catalyst amount, reaction temperature and hydrogen pressure, but is generally 1 to 8 hours.

Thus, according to the method of the present invention, it is possible not only to reduce the amounts of dibenzyl derivatives and red-colored by-products formed to 0.05% and to zero, respectively, but also to obtain DAS in a yield as high as more than 98%.

The present invention will be illustrated with reference to the following examples, which are only given for the purpose of illustration and not to be interpreted as limiting thereto.

In the examples, all parts and percents are expressed by weight unless otherwise indicated and, the purity of DAS was measured according to JIS K 4158 (1970), and the dibenzyl derivative was analyzed by liquid chromatography.

EXAMPLE 1

In an autoclave were placed 1,000 parts of dry DNS, 9,000 parts of absolute methanol and 20 parts of Raney nickel containing as little water as possible (water content 5 parts), and the reaction was carried out at $45° \pm 5°C$ under a hydrogen pressure of 1 to 7 kg/cm$^2$. Absorption of hydrogen was completed in one hour and a half. After filtering off the catalyst, methanol was distilled off to obtain 860 parts of DAS in a yield of 100% (purity 99.9%).

As another method of isolating the objective compound, the above filtrate free from the catalyst was acidified with a 2 N-hydrochloric acid to obtain 780 parts of 4,4'-diaminostilbene-2,2'-disulfonic acid (hereinafter referred to as "DAS-H") as white needles. Yield 99.4% and purity 99.8%. Dibenzyl derivatives were not detected.

In the same manner as mentioned above, the catalytic reduction was carried out except that DNS concentration of 30% and 20 parts of dry nickel were used instead. Yield 99.1% and purity 99.9%.

EXAMPLE 2

To an autoclave were added 2,040 parts of DNS (water content 2%), 8,000 parts of ethanol and 50 parts of Raney nickel (water content 25 parts) and the reaction was conducted at $55° \pm 3°C$ under a hydrogen pressure of 3 to 12 kg/cm$^2$. Absorption of hydrogen was completed in one hour and 40 minutes. After dissolving partially separated DAS in additional water, the reaction solution was acidified with a 2 N-hydrochloric acid to obtain 1,540 parts of greyish white DAS-H in a yield of 99.0% (purity 98.5%). Dibenzyl derivatives were not detected.

Decreasing the DNS concentration to 10%, the procedure was carried out in the same manner as mentioned above to obtain DAS-H in a yield of 98.9% (purity 98.5%).

EXAMPLE 3

In an autoclave were placed 2,220 parts of DNS (water content 10%), 8,000 parts of n-propyl alcohol and 50 parts of Urushibara nickel A (water content 40%) and the reduction was carried out at $50° \pm 3°C$ under a hydrogen pressure of 3 to 10 kg/cm$^2$. Absorption of hydrogen was completed in one hour and a half. The reaction mass was aftertreated in the same manner as described in Example 1 to give 1,540 parts of white DAS-H in a yield of 98.7% (purity 99.7%). Dibenzyl derivatives were not detected.

EXAMPLE 4

To an autoclave were added 1,500 parts of dry DNS, 8,500 parts of tert-butyl alcohol and 38 parts of Urushibara nickel A (water content 40%), and the reduction was carried out at $70° \pm 3°C$ under a hydrogen pressure of 5 to 15 kg/cm$^2$. Absorption of hydrogen was completed in one hour and 20 minutes. After dissolving partially separated DAS in additional water, the reaction solution was acidified with a 2 N-hydrochloric acid to obtain 1,149 parts of greyish white DAS-H in a yield of 98.2% (purity 97.0%). Dibenzyl derivatives were not detected.

EXAMPLE 5

A mixture comprising 250 parts of DNS (water content 20%), 3,000 parts of n-butyl alcohol containing 10% of water and 5 parts of Raney nickel (water content 50%) was heated to distill off a n-butyl alcohol-water fraction until the water content of the system was reduced to less than 3%. Then, the procedure was carried out in the same manner as described in Example 4 to give DAS-H (purity 99.4%) in a yield of 98.7%. Dibenzyl derivatives were not detected.

REFERENTIAL EXAMPLE 1

The hydrogenation was carried out in the same manner as described in Example 5 except that dehydration was not conducted. Then, the reaction product contained 68% of DAS-H and as by-products 7% of dibenzyl derivatives and 22% of red-colored products.

EXAMPLE 6

In an autoclave were placed 100 parts of DNS, 2.00 parts of Raney nickel W-6 (water content 40% and, as a buffer, 2.18 parts of potassium dihydrogen phosphate, 6.66 parts of disodium hydrogen phosphate and 900 parts of water. The pH of the system was 7.2. Then, hydrogenation was carried out at $155° \pm 5°C$ under a hydrogen pressure of 5 to 20 kg/cm$^2$. Absorption of hydrogen was completed in about 2.5 hours.

After cooling to room temperature, the Raney nickel was removed by filtration to obtain a yellow filtrate. DAS concentration of the filtrate was 8.7% (corresponding to yield of 100%), and dibenzyl derivatives and red-colored products were not detected.

On acidifying the filtrate with a 2 N-hydrochloric acid, 76 parts of greyish white DAS-H was obtained, while both dibenzyl derivatives and red-colored products were not detected. Yield 97% and purity 100%.

EXAMPLE 7

In an autoclave were added 200 parts of DNS, 4.0 parts of wet Urushibara nickel B and, as a buffer, 6.94 parts of boric acid, 1.64 part of sodium chloride, 4.58 parts of borax (Na$_2$B$_4$O$_7$.10H$_2$O) and 800 parts of water. The pH of the system was 8.1. On conducting hydrogenation at $160° \pm 5°C$ under a hydrogen pressure of 5 to 20 kg/cm$^2$, absorption of hydrogen was completed in about 2 hours and 20 minutes.

After cooling to room temperature, the nickel catalyst was removed by filtration to obtain a yellow filtrate. DAS concentration of the filtrate was 17.2% (yield 100%) and both dibenzyl derivatives and colored products were not detected.

EXAMPLE 8

In an autoclave were added 250 parts of DNS, 4.0 parts of wet Raney neckel W-7 and, as a buffer, 14.0 parts of potassium dihydrogen phosphate, 2.16 parts of sodium hydrogen carbonate and 750 parts of water. The pH of the system was 6.1. On conducting hydrogenation at $140° \pm 5°C$ under a hydrogen pressure of 10 to 25 kg/cm$^2$, absorption of hydrogen was completed in about 3 hours.

Aftertreatment was carried out in the same manner as described in Example 2 to obtain the reaction solution having a DAS concentration of 21.8% (corresponding to yield of 100%). Both dibenzyl derivatives and colored products were not detected.

On acidifying the solution with hydrochloric acid, DAS-H (purity 100%) was obtained in a yield of 96%.

REFERENTIAL EXAMPLE 2

In an autoclave were placed 150 parts of DNS, 2.40 parts of wet Raney nickel W-7 and 850 parts of water. The pH of the system was 8.1, and hydrogenation was then carried out at 70° ± 3°C under a hydrogen pressure of 10 to 30 kg/cm$^2$. After a theoretical amount of hydrogen was absorbed, the reaction solution was cooled to room temperature and filtered to remove the nickel catalyst. It was found from analysis that the red filtrate (pH 11) thus obtained contained neither DAS nor dibenzyl derivatives. On standing at room temperature, the red filtrate turned into a gelatinous matter with unknown structure.

REFERENTIAL EXAMPLE 3

The reduction process disclosed in Example 1 of Japanese Patent Publication No. 815/1973 was followed up, and it was found that the reduction stopped 18 hours after the beginning of reaction in spite of the presence of unreacted DNS. After filtering off the palladium catalyst, the filtrate obtained was measured on the content ratio between DAS, dibenzyl derivatives, and DNS recovered. It was found from the result that the ratio was 35 : 38 : 27 and further that DAS obtained was colored.

What is claimed is:

1. A process for preparing disodium 4,4'-diaminostilbene2,2'-disulfonate, which comprises reducing disodium 4,4'-dinitrostilbene-2,2'-disulfonate with hydrogen in the presence of a nickel metal catalyst in an aqueous medium at a temperature of 20° to 200°C in which the pH of the reaction system is adjusted to a range from 5 to 10 using a buffer.

2. The process according to claim 1, wherein the buffer is a composition of phosphoric acid, boric acid or organic acid series.

3. The process according to claim 1, wherein the nickel catalyst is a wet-developed nickel or dry nickel.

4. The process according to claim 3, wherein the wet-developed nickel is Raney nickel or urushibara nickel.

5. The process according to claim 1, wherein the nickel catalyst is used in an amount of at least 0.1% by weight based on the weight of disodium 4,4'-dinitrostilbene-2,2'-disulfonate.

6. The process according to claim 1, wherein the reducing is conducted under a hydrogen pressure of not higher than 30 kg/cm$^2$.

7. The process according to claim 1, wherein a concentration of disodium 4,4'-dinitrostilbene-2,2'-disulfonate is at least 1% by weight based on the weight of the reaction system.

* * * * *